United States Patent [19]

Palin et al.

[11] Patent Number: 4,699,186
[45] Date of Patent: Oct. 13, 1987

[54] LASER FILL-LEVEL INDICATOR FOR BLANK SYRINGES

[75] Inventors: Philip R. Palin, Sunnyvale; Bruce N. Watts, Santa Clara, both of Calif.

[73] Assignee: Collagen Corporation, Palo Alto, Calif.

[21] Appl. No.: 833,826

[22] Filed: Feb. 26, 1986

[51] Int. Cl.⁴ .............................................. B65B 3/04
[52] U.S. Cl. ................................ 141/2; 33/DIG. 21; 141/27
[58] Field of Search ................ 33/227, 228, 267, 274, 33/275 R, 286, 516, 520, 547, 573, DIG. 21; 73/293, 323; 141/1, 2, 25, 26, 27, 83, 94, 95, 311 R, 330, 383; 250/463.1, 465.1, 467.1, 574, 576, 577, 578; 350/112, 286, 433; 353/28, 40, 42; 356/36, 275

[56] References Cited

U.S. PATENT DOCUMENTS

| | | | |
|---|---|---|---|
| 1,737,126 | 11/1929 | Reyling et al. | 73/293 X |
| 3,045,495 | 7/1962 | Spencer et al. | 73/293 X |
| 3,728,027 | 4/1973 | Watanabe | 353/28 X |
| 3,907,009 | 9/1975 | Dobbins | 141/27 |
| 4,475,915 | 10/1984 | Sloane | 141/27 X |
| 4,490,919 | 1/1985 | Feist et al. | 33/DIG. 21 |
| 4,580,345 | 4/1986 | Andrew | 33/DIG. 21 |
| 4,589,738 | 5/1986 | Ozaki | 350/433 X |

FOREIGN PATENT DOCUMENTS 635284  1/1962  Canada .................. 353/40

Primary Examiner—Henry J. Recla
Assistant Examiner—Mark J. Thronson
Attorney, Agent, or Firm—Ciotti & Murashige, Irell & Manella

[57] ABSTRACT

A device for indicating the proper fill level for unmarked syringes is disclosed. This device employs the intersection of a perpendicular defracted sheet of low power visible laser light with the barrel of the syringe being filled as the indication of the proper fill level. A method of filling syringes which employs this device to indicate fill level is also disclosed.

7 Claims, 3 Drawing Figures

LASER FILL-LEVEL INDICATOR FOR BLANK SYRINGES

FIELD OF THE INVENTION

This invention relates to an improved apparatus for assisting in the filling of unmarked hypodermic syringes. In a preferred application this apparatus is employed in the filling of syringes with viscous collagen fluids.

BACKGROUND OF THE INVENTION

Many injectable medications and pharmaceutical preparations are distributed to the end user in prefilled hypodermic syringes. This unit dosage form is quick to use, has a high degree of sterility and allows easy control of the dose being administered.

It is very important that the fluid fill of these prepackaged materials be closely controlled -- usually to within a percent or two -- to assure proper dosing. With non-viscous fluids such as dilute solutions in water, this is often not a major problem, and the filling can be carried out automatically with a minimum of supervision and inspection. With viscous fluids there is often an air gap between the face of the syringe plunger and the face of the fluid itself as the fluid is added. This gap can be as much as 0.2-0.4 cc so that if the total fluid fill is in the range of a few cc's or less this gap can introduce a substantial error. This makes it necessary to visually monitor the actual position of the face of the fluid itself so as to be sure that the desired fill level is correctly achieved One way to indicate the desired fill level is to have it engraved or printed directly on the syringe barrel. This practice was prevalent with reusable glass syringes. It has fallen into some disfavor with many suppliers of prepackaged pharmaceutical preparations which employ substantial amounts of labeling information directly on the syringe body. Unmarked syringes (i.e., a syringe that has not been engraved or printed) have been created to allow the manufacturer flexibility in usage of the syringes for different products with different labeling. In addition, the labeling does not necessarily contain any indication of fill level and may be applied after filling of the unmarked syringe.

Thus, an apparatus is called for to quickly provide an accurate fill-level indication on unmarked syringe barrels. It is such an apparatus and a method for its use that the present invention provides.

STATEMENT OF THE INVENTION

It has now been found that the desired fill level for unmarked syringes can be quickly and precisely indicated with a syringe fill-level indicator which includes a laser capable of generating a low power visible laser beam, a refractor interposed in the laser beam which converts the laser beam into a two dimensional sheet of low power visible laser light, and a fitting for mounting the syringe to be filled in a position perpendicular to the sheet of laser light and in a position such that the barrel of the syringe intercepts the sheet of laser light at the desired fill level. The interception of the syringe body with the sheet of laser light results in a precise, sharp and very visible line to which the syringe is to be filled.

In another aspect this invention provides a method for filling a syringe with a viscous fluid to a predetermined fill level. This method involves affixing the syringe to a syringe fill-level indicator of the type just described; effecting a fluid-tight connection between the bore of the syringe and a supply of the viscous fluid; admitting a flow of the viscous fluid into the bore of the syringe; visually observing the level of fluid admitted into the bore, and when the level intersects the sheet of laser light provided by the fill-level indicator, stopping the flow of fluid and removing the filled syringe from the indicator and the supply of viscous fluid.

In yet another aspect, the invention is designed for use and easy maintenance in a clean-room environment. With this indicator, nothing touches the syringe. It allows the operator greater movement around the syringe and thereby minimizes possible contact and contamination by the operator. The present invention has advantages over a mechanical arm type level indicator which would be in close proximity to the syringe thereby complicating the syringe-fill process (i.e., the insertion of the sterile syringe into the sterile fill valve and the removal of the sterile syringe from the sterile fill valve once the syringe is filled). It is important to keep the syringe-fill process as simple as possible as it must be carried out by the operator 2,000-3,000 times a day in a sterile environment. In addition, the apparatus of the invention has the advantage that all of its external parts can be fabricated from materials such as metal, glass and plastics, for example DELRIN and the like, that are rust-proof, bacteria-proof and that can be easily cleaned and sterilized such as by autoclaving, etc.

In an application of particular interest, this indicator device and method of filling are used to fill syringes with fluids which include collagen.

DETAILED DESCRIPTION OF THE INVENTION

Brief Description of the Drawing

In this Detailed Description of the Invention, reference will be made to the drawings. In the drawings.

In these three figures, the same reference numerals are used in each to identify the same component.

DESCRIPTION OF THE PREFERRED EMBODIMENTS

Figure 1:
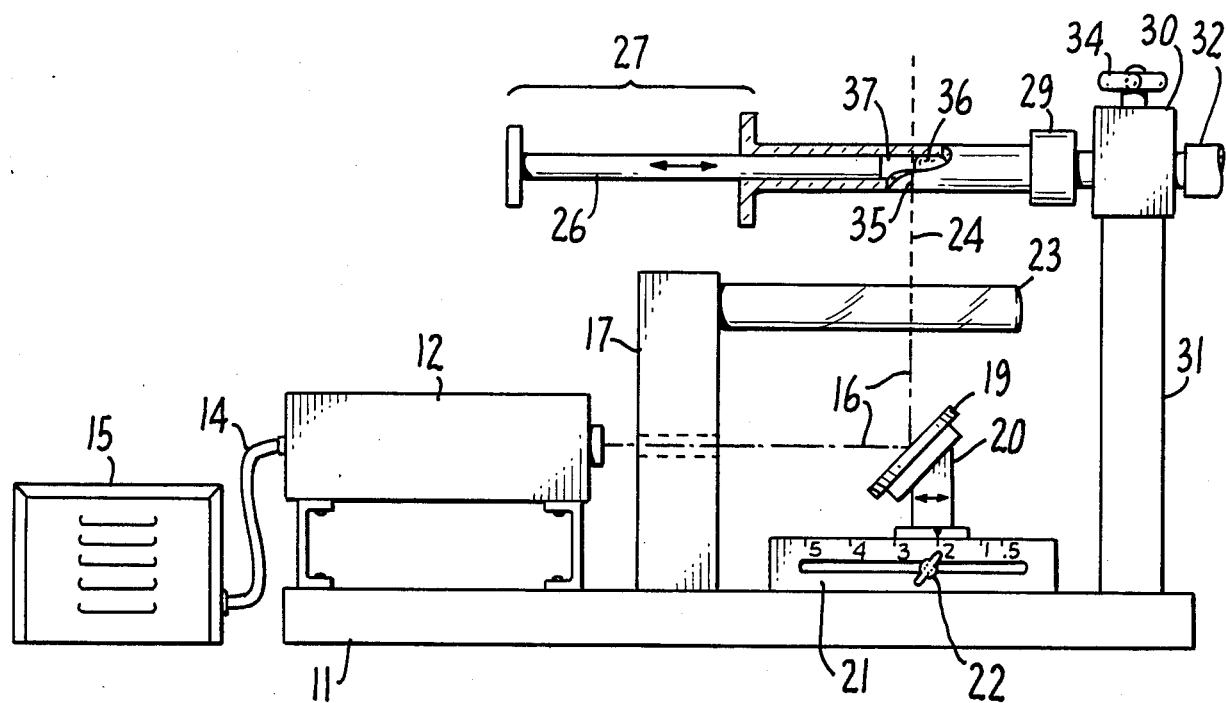
FIG. 1 is a partially cut-away elevational side view of one embodiment of the level indicator of the invention.
Figure 2:
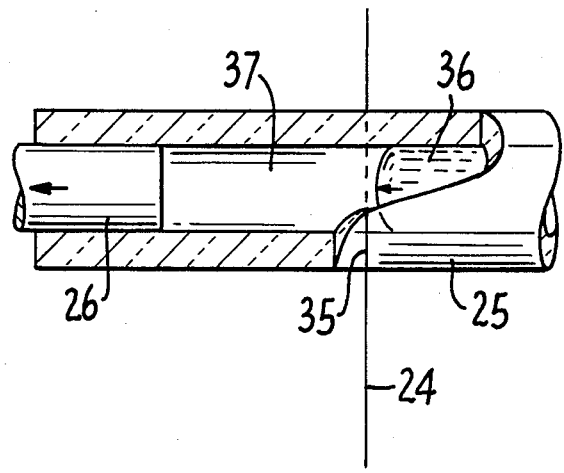
FIG. 2 is an expanded-scale, partially cut-away elevational side view of the level indication provided by the device of the invention which shows how the device may be employed in the context of filling a syringe with a viscous fluid.

Turning to all three figures together, a level-indicating device according to this invention is shown in FIG. 1 to include a baseplate 11 to which is attached a laser plasma tube 12. Power to drive the laser is provided via cable 14 from high voltage power supply 15. This laser has several characteristics. For one, it provides output in the visible wavelength range so as to permit the operator to see the level indication on the syringe body. For another, it is very low power. An output in the range of from about 0.01 milliwatt to about one milliwatt is adequate for purposes of this invention. Higher outputs are to be avoided. These higher outputs could lead to heating of the contents of the syringe. If the liquid is sensitive to heat, as is often the case with medically significant materials, this heating could be deleterious. Higher outputs are also to be avoided because they could be damaging to the eyes of the operators. At the outputs set forth above, and especially from about 0.001 milliwatt to about 0.1 milliwatt, a clear indication of the desired fill level is obtained and no special safety precautions need be taken. A helium-neon laser of 2 to 3 milliwatts output filtered down to about 0.1 milliwatts has proven very suitable.

The output beam 16 from plasma tube 12 passes through an aperture in support leg 17 and reflects off of mirror 19. Mirror 19 is a highly polished photo-quality mirror mounted on pedestal 20. Pedestal 20 is movable from side to side along track 21 and can be locked in position with set screw 22. When pedestal 20 is moved, it varies the lateral position of the reflected beam of laser light. Track 21 is depicted with graduations printed on its side and with an alignment point on the movable pedestal corresponding to the fill level that will be indicated. Beam 16 after reflecting off of mirror 19 passes through refractor 23. Refractor 23 can be a polished glass rod, suitably from about 8 to about 12 mm in diameter. This rod is aligned parallel to the syringe being filled and perpendicular to the reflected laser beam 16.

Figure 3:
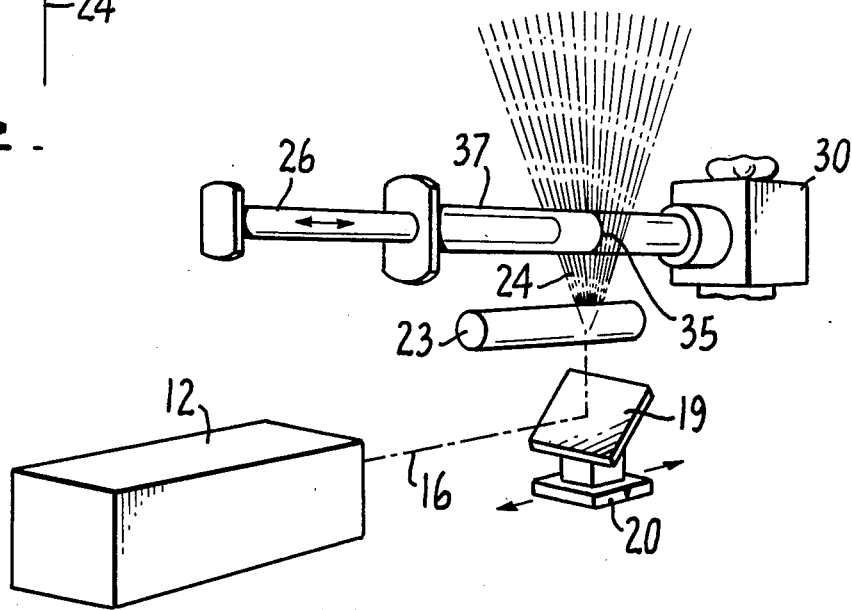
FIG. 3 is a schematic perspective view of the laser light path employed in the indicator device of this invention.

The refractor converts the laser beam into a two dimensional sheet of laser light 24. (This effect is shown more graphically in FIG. 3.) This sheet of coherent radiation contacts syringe barrel 25. Barrel 25 together with plunger 26 comprise the syringe being filled, syringe 27. Barrel 25 carries a luer lock 29 or other equivalent fitting which allows the syringe to be affixed into position parallel to the defractor rod 23 such as via filling valve 30, which is mounted to baseplate 11 with bracket 31, which is height adjustable for ease of operator use. Valve 30 communicates with fluid supply line 32 such that by moving valve handle 34 a flow of fluid can be delivered through valve 30 into barrel 25 of syringe 27. As is shown in detail in FIG. 3, the sheet of laser light 24 contacts barrel 25 and shows up as a clearly defined fine line 35 circling barrel 25. As the fluid 36 is pressured into syringe barrel 25, syringe plunger 26 is often slowly withdrawn or is pushed out by the incoming fluid. In the case of viscous fluids there is commonly an air gap 37 between the face of plunger 26 and the face of the incoming liquid 36. This air gap must be disregarded when determining the liquid fill level. The syringe is at proper fill when the face of the liquid reaches the laser light line appearing on the barrel. As the disposable syringes commonly in use today all employ transparent or translucent barrels, the operator can quickly and precisely see when the face of the inflowing liquid reaches the laser line. Fill accuracies of better than 1% can be achieved. When the desired degree of fill has been achieved, valve 30 is closed via handle 34 and the inflow of fluid is halted. Syringe 27 is then removed from the apparatus. The laser can remain on throughout this operation and no heating is noted and no risk of eye injury is posed to the operator by the low wattage laser.

The configuration of the apparatus shown in the figures can be varied if desired. For example, the initial laser beam does not need to be parallel to the refractor or to the syringe. It could come directly up from below or could come from behind or the like so long as the result of the refraction is a sheet of light perpendicular to the syringe body and intersecting the syringe body.

The device of this invention can be used to fill syringes to predetermined levels with any fluid. It finds special application, however, when the fluid being added is viscous. In our hands it finds especially preferred application in the filling of syringes with solutions and suspensions of collagen. Injectable collagen is a commerical product marketed by Collagen Corporation under the trademark Zyderm ™. Typical collagen solutions and suspensions are described in U.S. Pat. Nos. 3,949,073 and 4,424,208, which are incorporated herein by reference.

While this invention has been described with reference to a particular preferred embodiment, it will be appreciated by those skilled in the art that the invention shown in this embodiment can be varied without departing from its spirit and that the scope of the invention is as defined by the appended claims.

What is claimed is:

1. A syringe fill-level indicator comprising a laser capable of generating a low power visible laser beam, a refractor interposed in the laser beam which converts the laser beam into a two dimensional sheet of low power visible laser light, a syringe mounting fixture having a cylindrical orifice adapted for engaging the nozzle of the syringe to be filled, said orifice providing a valved inlet for fluid to the syringe nozzle into the syringe barrel, the axis of said orifice being perpendicular to the sheet of laser light and said fixture being positioned adjacent to the sheet of laser light and a syringe demountably engaged in the orifice such that the barrel of the syringe engaged in the orifice intercepts the sheet of laser light at the desired fill level.

2. The syringe fill-level indicator of claim 1 wherein the sheet of low power laser light is a vertical sheet.

3. The syringe fill-level indicator of claim 1 wherein the refractor is a transparent rod having a circular cross section at the point it is interposed in the laser beam.

4. A method for filling a syringe with a viscous fluid to a predetermined fill level which comprises affixing the syringe to a syringe fill level indicator itself comprising a laser capable of generating a low power visible laser beam, a refractor interposed in the laser beam which converts the laser beam into a two dimensional sheet of low power visible laser light, and means for fixing the syringe to be filled perpendicular to the sheet of laser light and in a position such that the barrel of the syringe intercepts the sheet of laser light at the desired fill level; effecting a fluid-tight connection between the bore of the syringe and a supply of the viscous fluid; admitting a flow of the viscous fluid into the bore of the syringe; observing the level of fluid admitted into the bore; and when the level intersects the sheet of laser light stopping the flow of fluid and removing the filled syringe from the indicator and the supply of viscous fluid.

5. The method of claim 4 wherein the means for fixing the syringe to be filled also effects the fluid-tight connection such that the fixing and effecting the connection are carried out in one step.

6. The method of claim 5 wherein the viscous fluid comprises collagen.

7. A method for filling a syringe with a liquid to a predetermined fill level which comprises affixing the syringe to a syringe fill level indicator itself comprising a laser capable of generating a low power visible laser beam, a refractor interposed in the laser beam which converts the laser beam into a two dimensional sheet of low power visible laser light, and means for fixing the syringe to be filled perpendicular to the sheet of laser light and in a position such that the barrel of the syringe intercepts the sheet of laser light at the desired fill line; effecting a fluid-tight connection between the bore of the syringe and a supply of the liquid; admitting a flow of the liquid into the bore of the syringe; observing the level of liquid admitted into the bore; and when the level intersects the sheet of laser light stopping the flow of liquid and removing the filled syringe from the indicator and the supply of liquid.

* * * * *